(12) United States Patent
Gobina et al.

(10) Patent No.: US 8,273,922 B2
(45) Date of Patent: Sep. 25, 2012

(54) PROCESS AND APPARATUS FOR THE PRODUCTION OF ALCOHOLS

(75) Inventors: Edward Gobina, Aberdeen (GB); Reuben Mfon Umoh, Aberdeen (GB)

(73) Assignee: The Robert Gordon University, Aberdeen (GB)

( * ) Notice: Subject to any disclaimer, the term of this patent is extended or adjusted under 35 U.S.C. 154(b) by 264 days.

(21) Appl. No.: 12/679,146

(22) PCT Filed: Sep. 19, 2008

(86) PCT No.: PCT/GB2008/003181
§ 371 (c)(1),
(2), (4) Date: Apr. 30, 2010

(87) PCT Pub. No.: WO2009/037469
PCT Pub. Date: Mar. 26, 2009

(65) Prior Publication Data
US 2010/0217051 A1    Aug. 26, 2010

(51) Int. Cl.
*C07C 29/153* (2006.01)
*B01J 20/28* (2006.01)

(52) U.S. Cl. .............................. 568/840; 502/4
(58) Field of Classification Search ................. 502/4
See application file for complete search history.

(56) References Cited

U.S. PATENT DOCUMENTS 4,921,823 A * 5/1990 Furneaux et al. ................. 502/4
6,488,838 B1 * 12/2002 Tonkovich et al. ........... 208/108
6,680,044 B1 * 1/2004 Tonkovich et al. ........... 423/652

* cited by examiner

*Primary Examiner* — Brian J Davis
(74) *Attorney, Agent, or Firm* — Hultquist, PLLC; David Bradin; Steven J. Hultquist

(57) ABSTRACT

A process utilising the gases carbon monoxide, carbon dioxide and hydrogen to produce alcohols directly, comprises the steps of bringing a fluid mixture comprising carbon monoxide, carbon dioxide and hydrogen into contact with the surfaces of a supported tubular porous catalyst membrane having a range of pore sizes including micropores, mesopores and macropores, controlling the temperature of the said catalyst membrane, maintaining a pressure over said catalyst membrane of from 88 to 600 kPa, and recovering alcohol containing product formed by contact of the fluid mixture with said catalyst membrane.

9 Claims, 2 Drawing Sheets

PROCESS AND APPARATUS FOR THE PRODUCTION OF ALCOHOLS

CROSS-REFERENCE TO RELATED APPLICATIONS

This application is a U.S. national phase application under the provisions of 35 U.S.C. §371 of International application No. PCT/GB08/03181 filed Sep. 19, 2008, which in turn claims Priority of Great Britain Patent application No. 0718398.1 filed Sep. 21, 2007. The disclosures of such international application and Great Britain priority application are hereby incorporated herein by reference in their respective entireties, for all purposes.

FIELD OF THE INVENTION

The present invention relates to an improved process for the production of products from gases, especially for obtaining alcohols directly. The invention also relates to a novel porous catalyst membrane for the direct conversion of carbon monoxide, carbon dioxide and hydrogen to beneficial products which are more readily transported and have potentially higher market value than the starting gaseous materials.

BACKGROUND TO THE INVENTION

Fixed bed, fluidised bed or stirred tank reactors are conventionally used for the synthesis of hydrocarbons from starting materials including carbon monoxide, carbon dioxide and/or hydrogen. The efficiency of existing fixed bed, fluidised bed and stirred tank reactors is limited by amongst other factors, mass transfer limitations and the creation of hot spots within the bed of catalyst.

Hot spots in a fixed catalyst bed promote conversion of carbon monoxide and/or carbon dioxide and hydrogen to methane, thereby reducing conversion to heavier hydrocarbons. Hot spots also cause catalyst deactivation.

Mass transfer limitations within catalysts in a fluidised bed or stirred tank reactor, reduce the effective rate of reaction and therefore rate of alcohol and aliphatic hydrocarbon production.

One means by which the mass transfer limitations can be reduced is by the means of a structured monolithic catalyst. U.S. Pat. No. 6,262,131 teaches that structured catalyst can have benefits in terms of activity and heat transfer for the conversion of gases to hydrocarbons but demonstrates that conventional structured catalyst typically has little effect on the selectivity of the reaction.

WO 98/38147 also describes how structured channel catalysts can be used to produce solely hydrocarbons by use of cobalt-containing catalysts.

It is known that higher alcohols can be produced by the use of cobalt catalyst co-precipitated with other metals, principally copper. Further, alkalisation increases the selectivity to alcohols (Today 65 (2001) 209-216, Arislete Dantas de Aquino, Antonio José Gomez Cobo). However elevated pressure is required to see any significant production of alcohols.

Conventional wisdom informs that cobalt on alumina produces a catalyst for the production of hydrocarbons. Thus, for example J. CHEM. SOC., CHEM. COMMUN., 1985 1179 "Selective Production of Alkenes and Alcohols on Cobalt Catalysts in the Liquid Phase", Michel Simon, André Mortreux, Francis Petit, Dominique Vanhove and Michel Blanchard, demonstrates that production of oxygenates does not exceed 10% under a wide range of conditions.

Furthermore, Applied Catalysis A: General Volume 186, Issues 1-2, 4 October. 1999, Pages 189-200, Martin Kraum and Manfred Baerns teaches that the effect of titania modification of the support is an increase in the dispersion of the catalyst and does not give an oxygenate-producing catalyst with cobalt.

At pressures as low as 10 bar, commercial practice for production of fuels in the 1940s, 90% selectivity to hydrocarbons was found.

Production of higher alcohols is known via the OXO process where high pressure hydroformylation is catalysed by homogeneous cobalt catalysts. However, this requires an alkenic feedstock as well as carbon monoxide and hydrogen.

SUMMARY OF THE INVENTION

The challenges associated with the fixed bed, fluidised bed and stirred tank reactors are generally well known. Accordingly, the present invention seeks to obviate or mitigate these problems, by providing a simple reactor, requiring less onerous conditions of use by virtue of a modified catalytic membrane component. The objects are achievable by the invention to be described hereinbelow, particularly by providing a means of obtaining a substantially isothermal catalyst system and by limiting the problems normally associated with mass transfer.

According to a first aspect of the invention, there is provided a process utilising the gases carbon monoxide, carbon dioxide and hydrogen to produce beneficial products directly, comprising the steps of:
(a) providing a supply of a fluid mixture comprising carbon monoxide, carbon dioxide and hydrogen;
(b) bringing said fluid mixture into contact with the surfaces of a supported porous catalyst membrane having a range of pore sizes;
(c) controlling the temperature of the said catalyst membrane;
(d) maintaining a pressure over said catalyst membrane of from 88 to 600 kPa;
(e) and recovering product formed by contact of the fluid mixture with said catalyst membrane.

The porous membrane may include micropores, mesopores and macropores in the range of pore sizes.

An advantage of the invention is that it provides for the direct conversion of the gases carbon monoxide, carbon dioxide and hydrogen to higher value products that are readily liquefied on cooling. In particular, the process permits direct formation of alcohols. These alcohols can be used as an additive component to increase the octane number of hydrocarbon fuels, typically performance improvers for petrol and diesel, or as commonly in demand raw materials in the petrochemical industry.

Typically, products having a carbon backbone of between two and nine carbon atoms are obtainable by this process.

These products include oxo-class products, particularly alcohols, and generally have the structure:

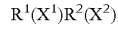

wherein $R^1$ is an aliphatic hydrocarbon chain, optionally branched, $X^1$ and $X^2$ which may be the same or different are independently selected from hydrogen (—H), a hydrocarbonyl (formyl) group (—CH=O), an oxo (keto) group (>C=O), or a hydroxyl group (—OH), and $R^2$ is a hydrocarbyl group such as methylene or higher alkyl, which are obtainable as products of this process.

Another advantage of the invention is that it provides for the one step direct conversion of the gases carbon monoxide, carbon dioxide and hydrogen to aliphatic hydrocarbons. These hydrocarbons can be used as fuels or as raw materials in the petrochemical industry.

The process conditions can be controlled to provide aliphatic hydrocarbons having a carbon backbone of at least five carbon atoms. Thus various higher alkanes are obtainable selectively.

Typically the fluid mixture useful in the process of the invention is a dry gas mixture (dew point typically below 30 degrees C.), which may consist essentially of carbon monoxide, carbon dioxide, hydrogen and is optionally substantially free of nitrogen, with no added oxygen or air. The fluid mixture supplied for the purposes of the process may also be substantially free of methane.

Typically the molar ratio of hydrogen to carbon monoxide is 2:1, and typically the molar ratio of carbon monoxide to carbon dioxide is 3:1.

By adopting a catalytic membrane structure, the advantages obtained include a reduction in mass transfer limitations, and an enhanced selectivity for the desired product. Thus it has not hitherto been recognised that a high selectivity for alcohols can be realised by operating a membrane system at low pressure with cobalt on alumina as the catalytic component.

Additionally, by utilising a membrane structure, a very short path length through the catalyst is obtained, that improves heat transfer, and reduces hot spot formation.

Furthermore, the catalytic membrane structure is highly suitable to design of a reactor that can operate at high conversions of carbon monoxide. Typically the conversion of carbon monoxide is over 80%.

Preferably the catalyst membrane is supported in a reactor adapted for heat and pressure control.

Typically means for monitoring the temperature and pressure within the reactor are provided.

The process may be conducted conveniently in the temperature range 180-350° C. Sufficient heat to maintain reaction may be generated by the exothermic reaction itself.

Suitably a reactant fluid mixture feed pressure will be in the range of up to 500 kPa, and typically upwards of 100 kPa, preferably at least 200 kPa.

Controllable means are provided for the supply of reactants and removal of products from the reactor.

The fluid mixture may be continuously supplied to contact the membrane, and the residence time of the reactant fluid mixture may be short, with products formed being continuously removed from the membrane. Any unreacted fluid mixture may be recovered and recycled. The recovery step may comprise liquefaction of products, and separation from gaseous unreacted fluid mixture.

Preferably the fluid mixture is supplied to a microporous surface of the catalyst membrane in a manner sufficient to ensure penetration of the micropores by said fluid mixture. The fluid mixture may flow from a first side of the microporous membrane to at least an opposed side of the membrane. The flow across the membrane may be accompanied by a flow along the length of the membrane.

Typically the process produces methane at a selectivity of less than 25%.

According to another aspect of the present invention there is provided a reactor for producing beneficial products from the gases carbon monoxide, carbon dioxide and hydrogen, comprising:

(a) a microporous catalyst membrane having a range of pore sizes supported within a reactor vessel;

(b) means for introducing a fluid mixture of carbon monoxide, carbon dioxide and hydrogen to the surfaces of the catalyst membrane;

(c) means to control temperature in the proximity of the membrane within the reactor;

(d) means to control pressure applied to the membrane within the reactor;

(e) means for recovering fluid from the reactor.

The form of the catalyst membrane may vary but a cylindrical form is convenient, and typically the catalyst membrane and reactor vessel are in tubular form, which facilitates flow-through processing, the membrane being positioned within the reactor vessel.

Preferably the temperature of the reaction is monitored by at least one thermocouple positioned adjacent to the catalyst membrane and a temperature indicating device attached to the thermocouple.

The temperature of the reaction vessel may be conveniently maintained between 180-350° C.

Addition and removal of heat from the reactor may be supplied by any suitable means, such as preheating of feed stock, heat transfer from liquid product, recycling of feed stock or products, provision of additional heat transfer surface area, and combinations thereof.

An electrical furnace may conveniently provide a source of heat for the reactor.

Preferably the furnace is positioned close to at least one external wall of the reaction vessel and operatively connected to the at least one thermocouple.

Preferably the pressure of the fluid in the reaction vessel is monitored using at least one pressure gauge.

The pressure within the reaction vessel may be up to about 500 kPa, and may be at least about 100 kPa, optionally at least 200 kPa.

Typically valves are used to control the supply of fluids to and from the reaction vessel.

According to another aspect of the present invention there is provided a porous catalyst membrane comprising:

(a) a porous support;

(b) active cobalt metal dispersed on the support;

(c) a portion of the support modified to provide a range of porosity including micropores, mesopores and macropores.

The support may comprise alpha alumina, but other supports are commercially available, e.g. silica, steel.

Optionally the modified portion of the support comprises a wash coat of a higher refractory material such as titania.

The wash coat is used advantageously to control porosity of the membrane and enhance the tortuosity of the membrane pores.

The alkalinity of selected supports can be used advantageously to control product distribution. Titania for example is alkaline and as a result the formation of oxygenates is favoured over aliphatic hydrocarbons. Titania also enhances the preferential adsorption of carbon dioxide over carbon monoxide. As a result, carbon dioxide can be inserted into the growing hydrocarbon chain leading to the formation of oxygenates.

Typically the catalyst is presented as a tubular membrane.

The catalyst may comprise other transition metals supported on the alumina.

The catalyst may comprise alkali metals supported on the alumina.

The catalyst may comprise any of the metals cobalt, iron and ruthenium, but preferably comprises cobalt as the principle active catalytic component:

Preferably cobalt accounts for at least 25% by weight of the catalyst precursor. Typically, the precursor is presented as a dispersion in which the cobalt accounts for at least about 3% by volume of the catalytic membrane.

The catalyst may include a promoter, particularly another metal which may be a transition metal, such as copper, or an alkali metal such as potassium, or both a transition metal and an alkali metal.

An advantage of the invention is that it provides a catalyst capable of catalysing the direct conversion of the gases carbon monoxide, carbon dioxide and hydrogen to alcohols and aliphatic hydrocarbons in a single step, using a simple apparatus at atmospheric pressure. The conversion of these gases to beneficial products in liquid form offers significant advantages for handling and transport, and solves many problems associated with these gases as oil production by-products.

Typically the temperature of the catalyst membrane is maintained in the range 180-350° C.

Typically the catalyst is capable of catalysing the conversion of carbon monoxide at over 80%.

According to another aspect of the present invention there is provided a method for producing a catalyst comprising the steps of:
(a) treating a controlled porosity refractory support with a catalyst precursor and then calcining the treated support to form supported active catalyst;
(b) optionally repeating step (a) for a sufficient number of repetitions to develop the active catalytic properties of the supported catalyst.

The support treatment step may comprise impregnating the support with a catalyst precursor.

The support may be pre-treated to control surface porosity, in particular to ensure that a range of pore sizes is obtained over at least a significant portion intended to receive a catalyst component.

Optionally, the support may be a refractory material that is treated with a higher refractory material prior to treating the support with catalyst precursor.

The support may be an alumina support such as alpha alumina, and the support may be prepared for use by applying a titania wash coat to at least a portion of the support. The titania wash coat may be applied by dip-coating the support with a titania sol.

Advantageously the titania wash coat helps control the temperature and residence time of fluid within the pores of the catalyst membrane.

Preferably the catalyst, which may comprise cobalt, is applied to the catalyst support by wet impregnation.

The introduction of the active catalyst components to the catalyst support may be accomplished by a number of pore penetrating methods, including dip/immersion or soaking in a salt fluid, optionally enhanced by application of pressure to enhance coating penetration, or by over-spraying with a salt fluid.

BRIEF DESCRIPTION OF THE DRAWINGS

An embodiment of the invention will now be described by way of example only and with reference to the accompanying drawings, in which:

Referring to FIG. 1 there is illustrated a reactor 1 consisting of a reaction vessel 2 into which is fed a fluid mixture of carbon monoxide, carbon dioxide and hydrogen via inlet port 3, through a wall 4 of the reaction vessel 2. A tubular porous catalyst membrane 5 is located in the reaction vessel 2. The ends of the tubular porous catalyst membrane 5 are sealed against the interior surface 6 of the reaction vessel 2 at interfaces 7. The reaction vessel 2 is heated using a furnace 8. The temperature of the interior 9 of the tubular porous catalyst membrane 5 is monitored and controlled using a thermocouple 10.

Figure 1:
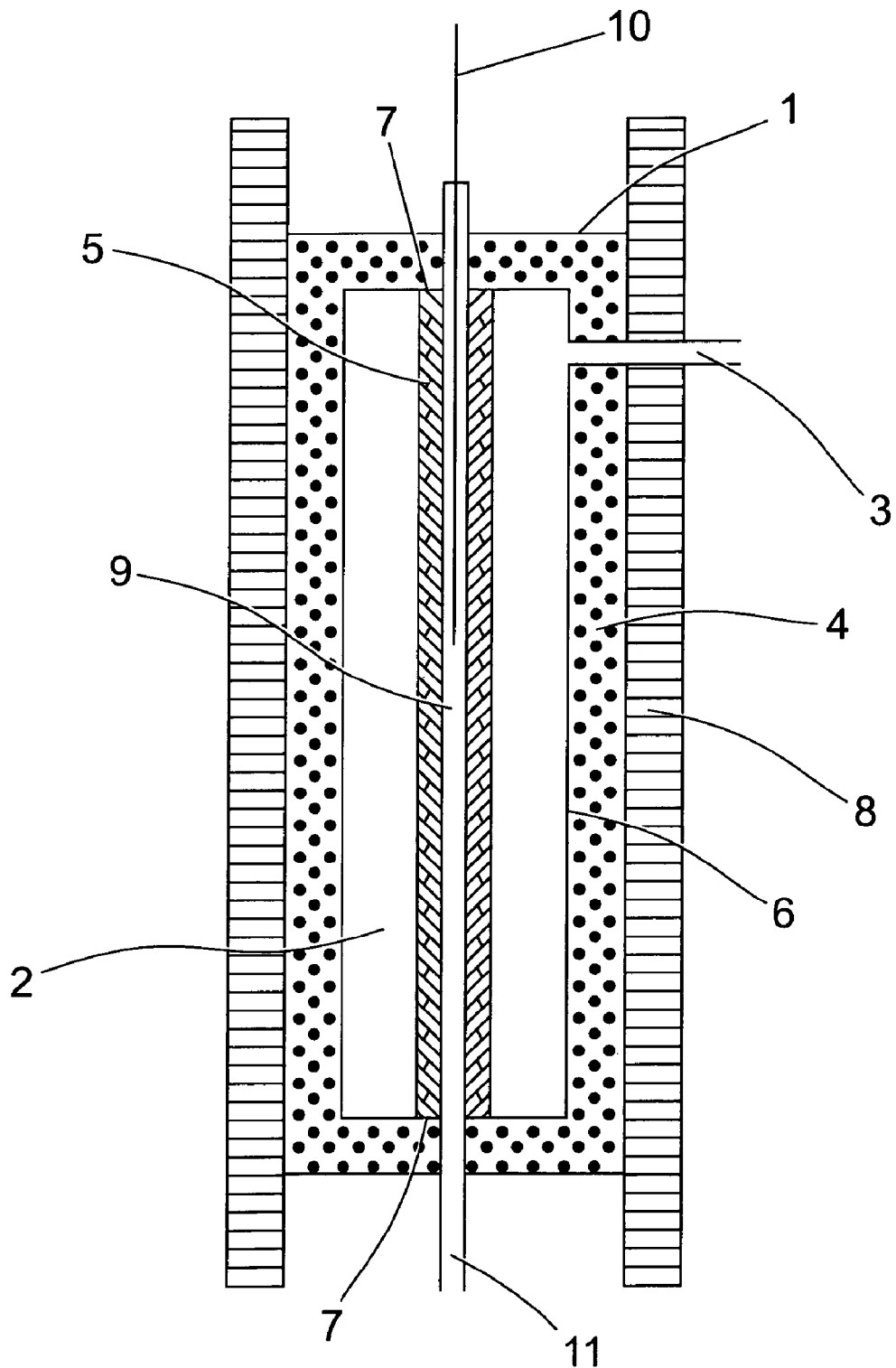
FIG. 1 illustrates a section through the reactor.

The fluid mixture of carbon monoxide, carbon dioxide and hydrogen supplied to the reaction vessel 2, moves through the porous catalyst membrane 5 into its interior 9. The exit port 11 allows for removal of liquid from the reactor 1.

Figure 2:
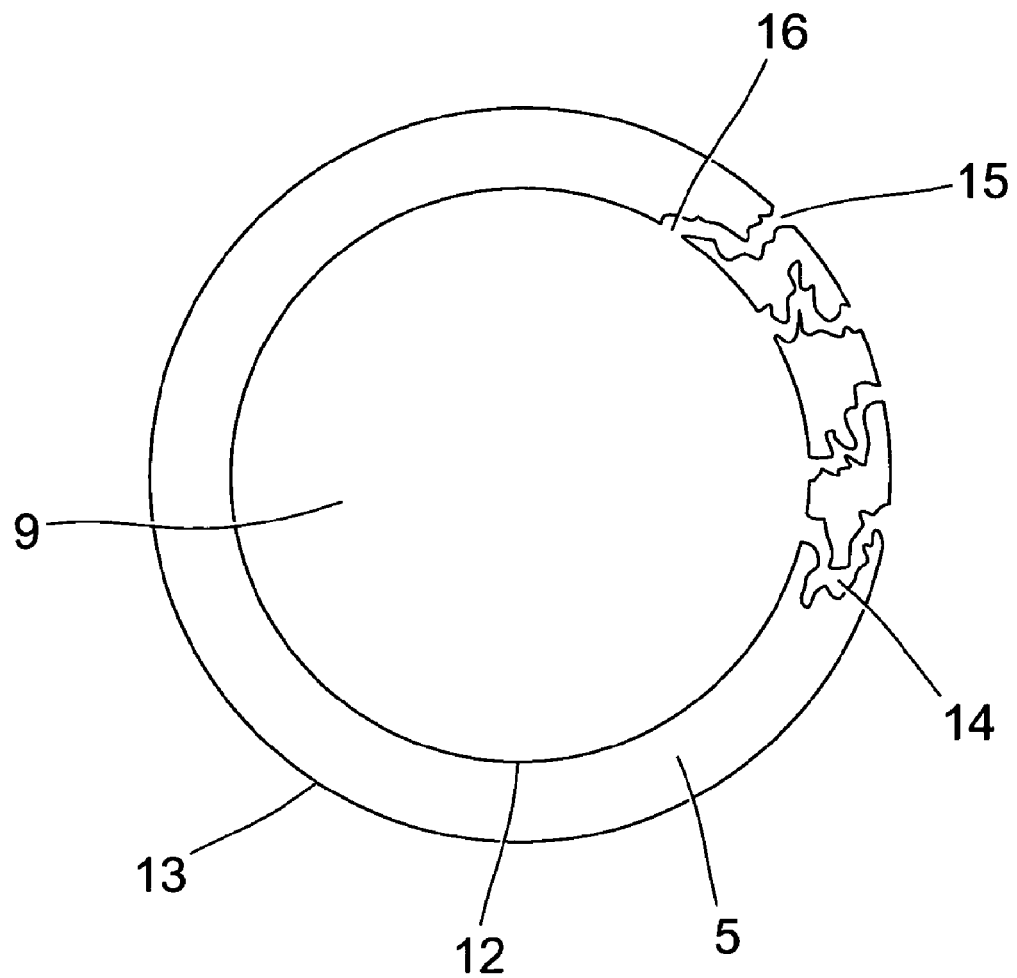
FIG. 2 illustrates a section through the porous catalyst membrane.

Referring to FIG. 2 there is illustrated a tubular porous catalyst membrane 5 with interior 12 and exterior 13 surfaces. Channels 14 in the porous catalyst membrane 5 have an opening 15 on the external surface and opening 16 on the internal surface.

MODES FOR PERFORMANCE OF THE INVENTION

The present invention will now be further described by way of the following illustrative examples.

EXAMPLE 1

Preparation of an Alumina-Supported Cobalt Catalyst.

The catalyst was prepared by the wet impregnation of a cylinder, 0.3 metres in length, 25 mm diameter, 2 mm thickness, formed of porous alpha-alumina to provide a catalyst support. The coated support was treated with 250 ml of an aqueous solution of cobalt nitrate. The catalyst was then air dried. The wet impregnation of the catalyst was then repeated, in this embodiment, using 250 ml of an aqueous solution of cobalt nitrate. The supported catalyst was then air dried and calcined in air for 5 hrs at 300° C.

The coated catalyst was then reduced in a hydrogen flow for 6 hrs.

EXAMPLE 2

Preparation of a Titania-Modified Alumina-Support

A catalyst support of the type described in example 1, is treated with a titania wash coat that is applied to at least a portion of the support. The titania wash coat is applied in this embodiment by dip-coating the support with a titania sol. The presence of the titania wash coat provides advantages in the eventual catalyst impregnated support by offering improved control of the temperature and residence time of fluid within the pores of the catalyst membrane.

EXAMPLE 3

Characterisation of an Alumina Supported Cobalt Catalyst.

Atomic adsorption spectroscopy and Energy-dispersive X-ray spectroscopy were used to calculate the percentage composition of cobalt in a sample of catalyst. The cobalt concentration in the catalyst was 2.34 wt %.

EXAMPLE 4

Processing Carbon Monoxide, Carbon Dioxide and Hydrogen.

The direct conversion of carbon monoxide, carbon dioxide and hydrogen to alcohols was achieved using a tubular membrane reactor.

The fluid mixture of carbon monoxide, carbon dioxide and hydrogen was supplied to the reactor via the inlet port at flow rate of 250 nmL/minute and a pressure of 102 kPa. The temperature of the membrane was maintained at 220° C. using an electric heating jacket.

The outlet port from the reactor directed the product stream from the space inside the tubular catalyst membrane to hot and cold traps. The temperature of the hot trap was maintained at 300° C.; the temperature of the cold trap was maintained at 0° C.

The fluid removed from the catalyst membrane was collected in a trap. Gaseous effluents were periodically analysed to determine the conversion of carbon monoxide, carbon dioxide and hydrogen and an analysis of the contents of the trap indicates selectivity to alcohols and aliphatic hydrocarbons obtained.

Table 1 indicates the typical product distribution of alcohols and aliphatic hydrocarbons obtained under standard operating conditions.

TABLE 1

| Product | Composition (Wt %) | Total (Wt %) |
|---|---|---|
| Alcohols | | |
| n-$C_5$ | 1.404 | 1.901 |
| i-$C_5$ | 0.497 | |
| n-$C_6$ | 13.536 | 15.048 |
| i-$C_6$ | 1.512 | |
| n-$C_7$ | 2.791 | 5.783 |
| i-$C_7$ | 2.992 | |
| n-$C_8$ | 9.080 | 11.885 |
| n-$C_8$ | 2.805 | |
| n-$C_9$ | 3.648 | 3.648 |
| Total | | 38.265 |
| Alkanes | | |
| $C_{10}$ | 0.381 | |
| $C_{11}$ | 1.080 | |
| $C_{12}$ | 0.320 | |
| Total | | 1.781 |

Example 5

Production of Alcohols at Varying Pressures:

A reactor feed consisting of a fluid mixture of carbon monoxide, carbon dioxide and hydrogen was supplied to a membrane reactor of the type described in Example 4, at a feed rate of 200 nmL/min. via the inlet port at various controlled pressures i.e., 200, 300, 400 and 500 kPa.

The reactor was maintained at 300° C., by means of an electrical heating jacket. The outlet port from the reactor directed the product stream from the space inside the tubular catalyst membrane to hot and cold traps. The temperature of the cold trap was maintained at 0° C. using ice.

The fluid collected from the catalyst membrane was collected in a trap. Gaseous effluents were periodically analysed to determine the conversion of carbon monoxide, carbon dioxide and hydrogen, and an analysis of the contents of the trap indicates the selectivity to alcohols and aliphatic hydrocarbons obtained.

Table 2 indicates the typical product distribution of alcohols and aliphatic hydrocarbons obtained under standard operating conditions.

TABLE 2

| Pressure (kPa) | Wt % Alcohols in liquid | Wt % Hydrocarbons in liquid |
|---|---|---|
| 200 | 9.3 | 2.2 |
| 300 | 7.2 | 1.6 |
| 400 | 25.6 | 6.5 |
| 500 | 18.2 | 3.9 |

Example 6

Production of Alcohols at Varying Temperatures

The fluid mixture of carbon monoxide, carbon dioxide and hydrogen was supplied to the reactor at 300 nmL/min via the inlet port at temperatures from 180 to 350 deg C. The reactor pressure was fixed at 4 bar (400 kPa). The outlet port from the reactor directed the product stream from the space inside the tubular catalyst membrane to hot and cold traps. The temperature of the cold trap was maintained at 0 deg C. using ice.

The fluid removed from the catalyst membrane was collected in a trap. Gaseous effluents were periodically analysed to determine the conversion of carbon monoxide, carbon dioxide and hydrogen and an analysis of the contents of the trap indicates the selectivity to alcohols and aliphatic hydrocarbons obtained.

Table 3 indicates the typical product distribution of alcohols and aliphatic hydrocarbons obtained under standard operating conditions.

TABLE 3

| Temperature ° C. | wt % Alcohols in liquid | wt % Hydrocarbons in liquid |
|---|---|---|
| 180 | 10 | 2.4 |
| 215 | 9.3 | 2.3 |
| 260 | 12.6 | 3.0 |
| 300 | 16.6 | 4.2 |
| 350 | 18.2 | 4.6 |

The invention claimed is:

1. A process utilizing the gases carbon monoxide, carbon dioxide and hydrogen to produce alcohols directly comprising the steps of:
    (a) providing a supply of a fluid mixture comprising carbon monoxide, carbon dioxide and hydrogen;
    (b) bringing said fluid mixture into contact with the surfaces of a supported porous catalyst membrane having a range of pore sizes;
    (c) controlling the temperatures of the said catalyst membrane;
    (d) maintaining a pressure over said catalyst membrane of from 88 to 600 kPa;
    (e) and recovering product formed by contact of the fluid mixture with said catalyst membrane.

2. A process according to claim 1, wherein the catalyst membrane is supported as a tubular structure.

3. A process according to claim 1, wherein the range of pore sizes includes micropores, mesopores and macropores.

4. A process according to claim 1, wherein the molar ratio of hydrogen to carbon monoxide is 2:1.

5. A process according to claim 1, wherein the molar ratio of carbon monoxide to carbon dioxide is 3:1.

6. The processs of claim 1, wherein the process is carried out in a reactor comprising:
    (a) a microporous catalyst membrane having a range of pore sizes supported within a reactor vessel;

(b) means for introducing a fluid mixture of carbon monoxide, carbon dioxide and hydrogen to the surfaces of the catalyst membrane;
(c) means to control temperature in the proximity of the membrane within the reactor;
(d) means to control pressure applied to the membrane within the reactor;
(e) means for recovering fluid from the reactor.

7. The process according to claim 6, wherein the catalyst membrane is supported as a tubular structure.

8. The processs of claim 1, wherein the porous catalyst membrane comprises:
(a) a porous support;
(b) one or more active cobalt, iron, or ruthenium metals dispersed on the support;
(c) a portion of the support modified to provide a range of porosity including micropores, mesopores and macropores.

9. The process of claim 8, wherein the metal is cobalt.

* * * * *